(12) United States Patent
Schmidt

(10) Patent No.: US 9,586,879 B2
(45) Date of Patent: Mar. 7, 2017

(54) PROCESS FOR THE SELECTIVE PRODUCTION OF PROPANOLS BY HYDROGENATION OF GLYCEROL

(71) Applicant: W. R. GRACE & CO.-CONN., Columbia, MD (US)

(72) Inventor: Stephen R. Schmidt, Silver Spring, MD (US)

(73) Assignee: W. R. GRACE & CO-CONN., Columbia, MD (US)

(*) Notice: Subject to any disclaimer, the term of this patent is extended or adjusted under 35 U.S.C. 154(b) by 0 days.

(21) Appl. No.: 14/774,792

(22) PCT Filed: Mar. 14, 2014

(86) PCT No.: PCT/US2014/027378
§ 371 (c)(1),
(2) Date: Sep. 11, 2015

(87) PCT Pub. No.: WO2014/152472
PCT Pub. Date: Sep. 25, 2014

(65) Prior Publication Data
US 2016/0031777 A1    Feb. 4, 2016

Related U.S. Application Data

(60) Provisional application No. 61/790,690, filed on Mar. 15, 2013.

(51) Int. Cl.
C07C 29/60    (2006.01)
C07C 31/10    (2006.01)
(Continued)

(52) U.S. Cl.
CPC .............. *C07C 29/60* (2013.01); *C07C 31/10* (2013.01); *B01J 21/02* (2013.01); *B01J 23/72* (2013.01); *B01J 23/80* (2013.01)

(58) Field of Classification Search
CPC ........................................................ C07C 29/60
See application file for complete search history.

(56) References Cited

U.S. PATENT DOCUMENTS

| | | | |
|---|---|---|---|
| 1,628,190 A | 5/1927 | Raney | 502/301 |
| 1,915,473 A | 6/1933 | Raney | 502/301 |

(Continued)

FOREIGN PATENT DOCUMENTS

| | | | |
|---|---|---|---|
| DE | 524101 | 5/1931 | |
| EP | 0523015 | 1/1993 | C07C 31/20 |

(Continued)

OTHER PUBLICATIONS

Montassier et al., in Bulletin De La Societe Chimique De France vol. 1989, Issue No. 2, pp. 148-155.

(Continued)

*Primary Examiner* — Paul A Zucker
*Assistant Examiner* — Medhanit Bahta
(74) *Attorney, Agent, or Firm* — Charles A. Cross

(57) ABSTRACT

The present invention discloses a process for the selective hydrogenation of glycerol in the liquid phase to produce 1- and 2-propanols in high yields as the major organic products. The process comprises subjecting a glycerol stream having at least 30% by weight water to a combination of low pressure and high temperature hydrogenation conditions in the presence of a promoted or un-promoted skeletal copper catalyst.

21 Claims, 2 Drawing Sheets

(51) Int. Cl.
  *B01J 23/80* (2006.01)
  *B01J 21/02* (2006.01)
  *B01J 23/72* (2006.01)

(56) References Cited

U.S. PATENT DOCUMENTS

| | | | |
|---|---|---|---|
| 2,139,602 A | 12/1938 | Raney | 23/238 |
| 2,461,396 A | 2/1949 | Raney | 75/0.5 |
| 2,977,327 A | 3/1961 | Raney | 252/472 |
| 4,826,799 A | 5/1989 | Cheng et al. | 502/301 |
| 5,616,817 A | 4/1997 | Schuster et al. | 568/861 |
| 7,355,083 B2 | 4/2008 | Tuck et al. | |
| 7,754,928 B2 | 7/2010 | Manzer | 568/903 |
| 7,790,937 B2 * | 9/2010 | Henkelmann | C07C 29/60 568/861 |
| 8,080,692 B2 | 12/2011 | D'Hondt et al. | 568/861 |
| 8,101,807 B2 | 1/2012 | Bricker et al. | 568/852 |
| 8,239,951 B2 | 8/2012 | Lotem et al. | 726/25 |
| 8,271,924 B1 | 9/2012 | Orthner et al. | 716/117 |
| 8,273,924 B2 | 9/2012 | Henkelmann et al. | 568/861 |
| 8,283,504 B2 | 10/2012 | Morizane et al. | 568/881 |
| 8,329,436 B2 | 12/2012 | Verser et al. | 435/165 |
| 2003/0203812 A1 | 10/2003 | Ostgard et al. | B01J 25/00 |
| 2004/0260120 A1 | 12/2004 | Ostgard et al. | 562/538 |
| 2007/0099161 A1 | 5/2007 | Krebs et al. | 434/322 |
| 2007/0149830 A1 | 6/2007 | Tuck et al. | 568/861 |
| 2008/0045749 A1 | 2/2008 | Arredondo et al. | |
| 2009/0012334 A1 | 1/2009 | Hulteberg et al. | 568/903 |
| 2011/0015450 A1 | 1/2011 | Morizane et al. | 568/881 |
| 2011/0071323 A1 | 3/2011 | Stankowiak et al. | 568/852 |
| 2011/0313211 A1 | 12/2011 | Schmidt | 568/861 |
| 2012/0330070 A1 | 12/2012 | Suppes | 568/862 |

FOREIGN PATENT DOCUMENTS

| | | | |
|---|---|---|---|
| EP | 2565175 | 3/2013 | C07C 29/60 |
| WO | 2007099161 | 9/2007 | C07C 29/60 |

OTHER PUBLICATIONS

R. Connor and H. Adkins in J. Am. Chem. Soc. 54, 1932, pp. 4678-4690.
M. A. Dasari et al., in Appl. Chem. A: General 281, 2005, pp. 225-231.
Chaminand et al., in Green Chem. 6, 2004, pp. 359-361.

* cited by examiner

PROCESS FOR THE SELECTIVE PRODUCTION OF PROPANOLS BY HYDROGENATION OF GLYCEROL

CROSS-REFERENCE TO RELATED CASES

This application claims the benefit of the filing date of International Application No. PCT/US2014/027378 filed Mar. 14, 2014, and U.S. Provisional Patent Application No. 61/790,690 filed Mar. 15, 2013, the disclosure of which is hereby incorporated by reference.

FIELD OF THE INVENTION

The present invention relates to a process for the selective hydrogenation of glycerol in the liquid phase. More particularly, the present invention relates to the selective hydrogenation of glycerol in the liquid phase whereby propanols are produced in high yields as the major liquid phase product.

BACKGROUND OF THE INVENTION

Glycerol is becoming an abundant chemical product as industry and consumers become increasingly reliant on fuels from biological sources. In particular, fuels (also known as biofuels) are being made from biogenic fat- or oil-containing sources and used oils obtained, for example, from cooking oil waste from restaurants and waste animal fats from food-related processing plants. Diminishing supply of readily available traditional petroleum sources, increasing prices of petroleum feeds and concerns of their impact on the environment are driving increased demands for alternative fuels such as biofuels.

To this end, hydrogenation processes for the conversion of glycerol to 1,2-propanediol have been extensively studied in recent years, and high yields have been obtained in some cases. Various catalysts have been used in these processes, including copper.

Chaminand et al., in Green Chem. 6, 2004, pages 359-361, describe the hydrogenation of aqueous glycerol solutions at 180° C. and 80 bar hydrogen pressure in the presence of supported metal catalysts based on Cu, Pd and Rh. Copper chromite, copper zinc oxide, copper aluminum oxide and copper silicon dioxide are mentioned as catalysts for such processes. Indeed, it is widely known that copper chromite is a suitable catalyst in the hydrogenation of glycerol. Copper chromite, however, is an oxide that is prone to chemical and physical degradation relative to metallic catalysts.

M. A. Dasari et al., in Appl. Chem. A: General 281, 2005, pages 225-231, describe a process for the low-pressure hydrogenation of glycerol to propylene glycol (1,2-propane diol) at a temperature of 200° C. and a hydrogen pressure of 200 psi (13.79 bar) in the presence of a nickel, palladium, platinum, copper, or copper chromite catalyst.

German Patent 524 101 has been attributed as describing a process in which glycerol is subjected to a gas-phase hydrogenation in the presence of a hydrogenation catalyst and hydrogen in considerable excess. Copper and/or cobalt catalysts can be used for the hydrogenation of glycerol. See U.S. Pat. No. 7,355,083 and WO 2007/099161. R. Connor and H. Adkins, in J. Am. Chem. Soc. 54, 1932, pages 4678-4690, describe the hydrogenolysis of oxygen-containing organic compounds, such as glycerol, to 1,2-propanediol in the presence of a copper-chromium-barium oxide catalyst.

C. Montassier et al., in Bulletin de La Societe Chimique de France 1989, No. 2, pages 148-155, describe investigations into the reaction mechanism of the catalytic hydrogenation of polyols in the presence of various metallic catalysts, such as, for example, hydrogenation of glycerol in the presence of copper.

EP 0 523 015 describes a process for the catalytic hydrogenation of glycerol for the preparation of 1,2-propanediol and 1,2-ethanediol in the presence of a Cu/Zn catalyst at a temperature of at least 200° C. In this process, the glycerol is used as an aqueous solution having a glycerol content of from 20 to 60% by weight, the maximum glycerol content in the working examples being 40% by weight.

U.S. Pat. No. 5,616,817 describes a process for the preparation of 1,2-propanediol by catalytic hydrogenation of glycerol at elevated temperature and super-atmospheric pressure, in which glycerol having a water content of not more than 20% by weight is reacted in the presence of a catalyst which comprises from 40 to 70% by weight of cobalt, if appropriate, manganese and/or molybdenum and a low copper content of from 10 to 20% by weight. The temperature is in the range of from about 180 to 270° C. and the pressure in a range of from 100 to 700 bar, preferably from 200 to 325 bar.

U.S. Patent Publication No. 2008/0045749 discloses a two step process in manufacturing 1,2-propanediol from glycerol in which the glycerol is first subjected to a dehydrogenation reaction to produce a carbonyl compound, hydroxyacetone. The second step can comprise hydrogenating the acetone to 1,2-propanediol.

U.S. Pat. No. 8,273,924 B2 which discloses the catalytic hydrogenation of glycerin with a water content of less than 20% by weight to give a 92% yield of 1,2-propanediol. The conversion of glycerol was achieved through the use of hydrogenation catalysts supported on silica, with the active composition comprising nickel, copper, and manganese. The hydrogenation reaction is carried out at a pressure and temperature range of 100 to 700 bar and 180 to 270° C., respectively. N-propanol, isopropanol and other lower alcohols were obtained as by-products.

A skeletal copper catalyst has also been used as a catalyst for the hydrogenation of glycerol to 1,2-propanediol. For example, U.S. Patent Publication No. 2011/0071323 A1 discloses a method for producing 1,2-propanediol from the catalytic hydrogenation of glycerin in a reactor operated at a steady-state conversion of preferably 60 to 95%. Glycerin is reacted with hydrogen in the presence of a copper containing, powdered catalyst in a liquid phase in a continuous stirred reactor at a pressure of 50 to 90 bar and reaction temperatures ranging from 180 to 240° C. Catalysts mentioned were Raney® copper or CuO/ZnO. 1,2-propanediol was obtained in high selectivity of up to 97% with n-propanol, isopropanol and ethanol being detected in small amounts as byproducts.

Byproducts of the glycerol hydrogenolysis to 1,2-propanediol have included 1-propanol and 2-propanols which are also useful chemicals. 1-propanol has been produced via hydroformylation of ethylene and is used mainly as a solvent, a printing ink and a chemical intermediate for the production of n-propyl acetate. See J. D. Unruh et. al., Kirk-Othmer Encyclopedial of Chemical Technology, John Wiley & Sons, NY, 2000. 2-propanol (isopropanol) has been produced by the hydration of propylene and used mainly as a solvent.

Consequently, it is desirable to provide processes for the hydrogenation of glycerol which are highly selective for 1- and/or 2-propanols and which provide these alcohols in high yield as the major products.

SUMMARY OF THE INVENTION

It has now been found that, surprisingly, glycerol-containing streams having a high water content can be subjected to a low pressure, high temperature hydrogenation to give 1-propanol and/or 2-propanol as the major products in high yields and high selectivity.

Accordingly, the present invention provides a process for selectively producing 1-propanol and 2-propanol in a high yield and high selectivity by reacting a liquid phase which comprises about 70% by weight or less glycerin and at least about 30% by weight water with hydrogen in the present of a skeletal copper catalyst at a temperature of greater than about 250° C. and a pressure of less than 100 bar (less than about 1470 psig).

In another embodiment of the present invention is provided a process for hydrogenation of glycerol in which a feed comprising glycerol having a water content of at least about 30% is contacted with hydrogen and subjected to hydrogenation in the liquid phase in the present of a skeletal copper catalyst at a temperature of greater than about 250° C. and a pressure of less than 100 bar. These and other aspects and embodiments of the present invention are described in further details below.

DETAILED DESCRIPTION OF THE INVENTION

Figure 1:
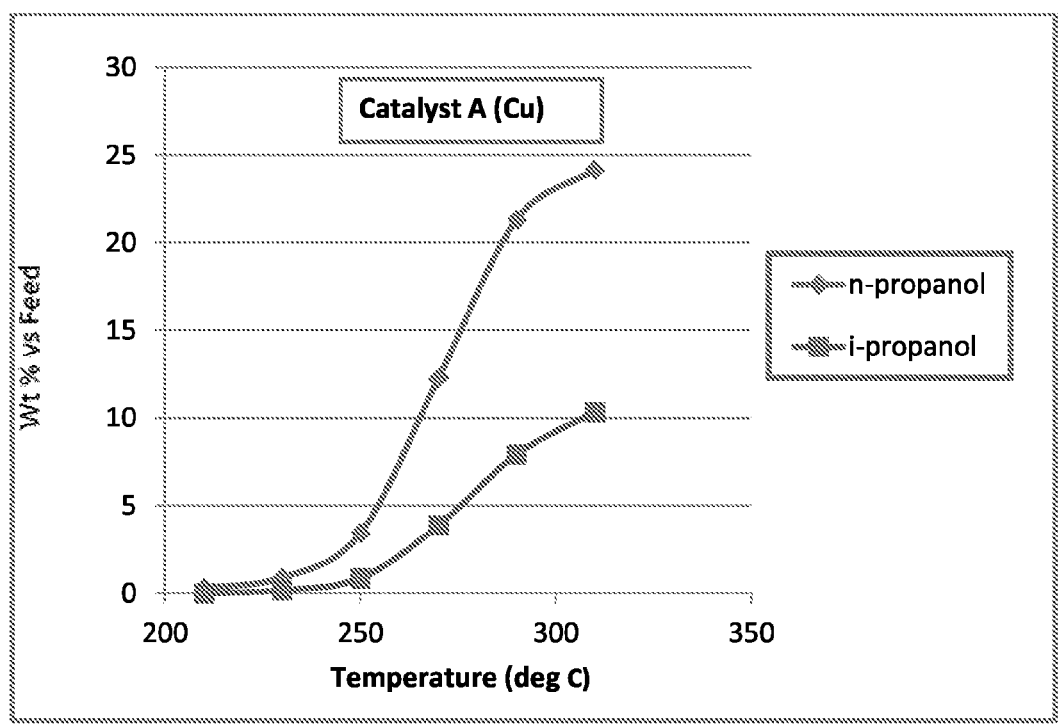
FIG. 1 is a graphic representation of the product yield of propanols as a function of temperature using an unpromoted skeletal copper catalyst.
Figure 2:
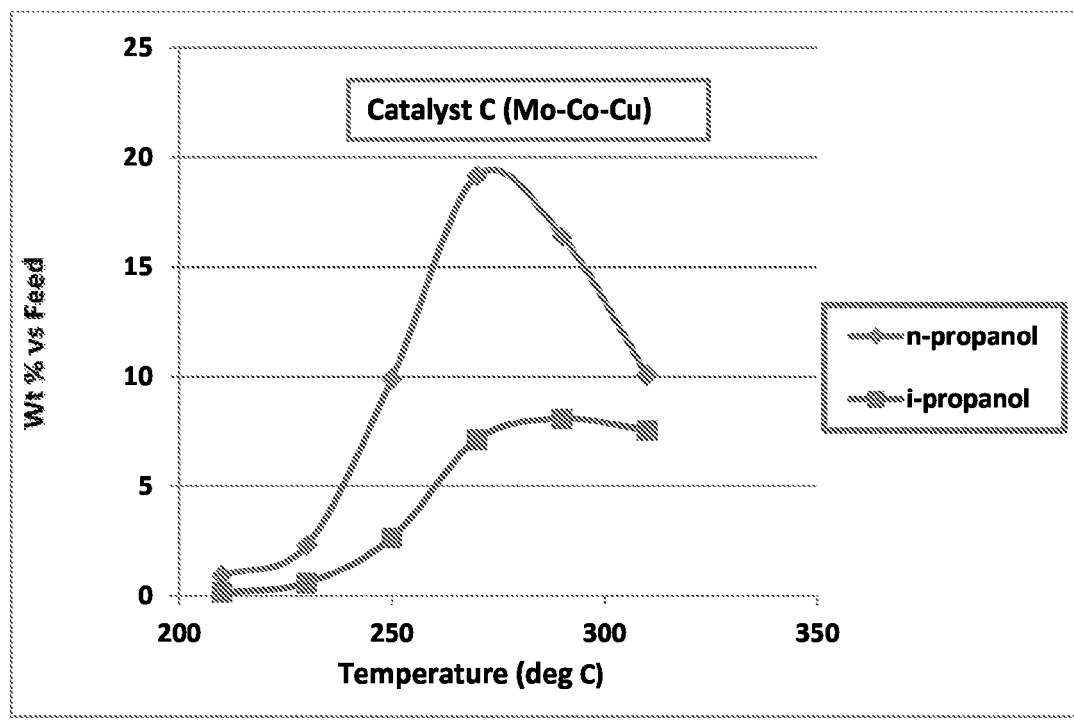
FIG. 2 is a graphic representation of the product yield of propanols as a function of temperature using a Mo and Co promoted skeletal copper catalyst.

For purposes of this invention the term "propanol" or "propanols" is used herein to collectively indicate 1-propanol and 2-propanol.

For purposes of this invention the terms "glycerol" and "glycerin" are used herein interchangeably to indicate the compound ($CH_2OH$)CHOH($CH_2OH$), i.e. 1,2,3-propanetriol.

The process of this invention is generally suitable for making 1- and 2-propanol from a glycerol-containing stream. Suitable glycerol streams can include reagent grade glycerin, as well as glycerol byproduct streams from industrial processes. These latter streams include glycerol-containing streams from the processing of oil- and/or fat-containing starting materials, for example from soap production, fatty acid and fatty acid ester production, etc. The glycerol-containing feed stream that is becoming more prevalent is that obtained in the preparation of alkyl esters of higher fatty acids by transesterification of fatty acid triglycerides, such as that obtained in the production of "biodiesel".

Glycerol-containing streams to be processed by this invention preferably have a water content of at least about 30% by weight, preferably at least about 40% by weight. In one embodiment of the invention a water content of at least about 50% by weight is particularly suitable. The use of glycerol-containing streams having water content in the range of the invention permits the preparation of 1- and 2-propanol in high yields and with high selectivity at the temperature and pressure range of the present invention. It is possible to use glycerol-containing streams containing higher amounts of water, and achieve relatively high yields and high selectivity for propanols, but processing such streams is less economical because of reduced space-time yield due to dilution of the desired feedstream. Nevertheless, a water content in the general range of about 30% by weight to about 70% by weight is particularly suitable, with the a water content in the range from about 40% to about 60% by weight, being especially suitable for maintaining a suitable dilution and viscosity for the glycerol stream during the hydrogenation.

While not preferable, the glycerol-containing streams may include glycerol-miscible organic solvent instead of or in addition to water. Such glycerol-containing streams would preferably have a total solvent content of no more than 20% by weight, particularly preferably no more than 10% by weight of the stream. If solvent is used in addition to water, the solvent in the solvent/water mixture is preferably not more than 50% by weight, particularly preferably not more than 20% by weight, based on the total weight of the solvent/water mixture. Suitable glycerol-miscible organic solvents are $C_1$ to $C_4$-alkanols, such as methanol, ethanol, n-propanol, isopropanol, n-butanol, tert-butanol, polyols and mono- and dialkyl ethers thereof, cyclic ethers, such as dioxane and tetrahydrofuran, etc. Other suitable solvents are aromatic hydrocarbons, such as benzene, toluene or the xylenes.

The glycerol-containing streams may be subjected to conditioning processes prior to hydrogenation, including purification processes to remove undesired components and/or water and organic solvent. Glycerol-containing feedstreams, for example, may comprise inorganic salts and catalyst poisons, i.e. components which adversely affect (e.g., deactivate) the hydrogenation catalyst, and/or which adversely affect processes conducted on the diol product of this invention downstream, e.g., distillation to purify the 1,2-propanediol product. Catalyst poisons include, for example, nitrogen-containing compounds, such as amines, and sulfur-containing compounds, such as sulfuric acid, hydrogen-sulfide, thioalcohols, thioethers, e.g., dimethyl sulfide, carbon oxide sulfide, amino acids, e.g. amino acids comprising sulfur and additional nitrogen groups, fatty acids and salts thereof. The catalyst poisons may further include halogen compounds, traces of conventional extracting agents, e.g. acetonitrile or N-methylpyrrolidone, etc. and, if appropriate, organic phosphorus and arsenic compounds. A catalyst poison frequently present in glycerol-containing streams from oil and fat refining is sulfuric acid, which is used as a catalyst in an esterification step upstream. Similarly sodium hydroxide, potassium hydroxide or other sodium or potassium salts such as carbonates and sulfates may be present due to upstream transesterification processes. Processes to remove these contaminants are well known, and include thermal treatments, distillation, adsorption, ion exchange, membrane separation, or a combination of two or more of these methods. Membrane separation methods employ membranes having selective pore sizes for reducing the water content and/or salt removal.

Adsorbents chosen to treat the glycerol-containing streams to remove components which adversely affect the catalytic hydrogenation generally have a specific surface area, determined according to BET, in the range of from about 10 to 2000 $m^2/g$, preferably in the range of from 10 to 1500 $m^2/g$, more preferably in the range of from 10 to 400 m²/g, especially in the range of from 60 to 250 m²/g. Suitable adsorbents are, for example, activated aluminas, e.g., those that are prepared from aluminum hydroxide, which is obtainable from aluminum salt solutions by conventional precipitation methods. Active aluminas suitable for the process according to the invention are also obtainable starting from aluminum hydroxide gels. Suitable adsorbents also include alumina-containing solids, which include clay. Other suitable adsorbents are aluminum phosphates, silica, titania, zirconia, and activated carbon.

The glycerol-containing stream may also be subjected to a catalytic desulfurization, if appropriate in the presence of hydrogen, for reducing the contents of sulfur-containing compounds, especially sulfur-containing aromatic compounds. Suitable desulfurization agents are described in US Patent Application 2007/099161, the contents of which are incorporated by reference.

The configuration of process equipment for carrying out one or more of the aforementioned conditioning processes is well within the skill of those skilled in the art. It is also well known how one would configure these processes in connection with a hydrogenation reaction.

The glycerol-containing streams according to the invention preferably originate from the production of fatty acid mono-alkyl esters that are obtained from biogenic oil- and/or fat-containing starting mixtures and can be used as fuel in diesel engines. US Patent Application 2007/099161, the contents of which are incorporated herein by reference, describes suitable types of biogenic materials from which glycerol may originate.

Preferably, the glycerol-containing stream is produced in the following general process: (1) providing a biogenic fat- and/or oil-containing starting mixture, (2) transesterification of the fatty acid triglycerides present in the starting mixture with at least one monoalcohol and, if appropriate, esterification of the free fatty acids present in the starting mixture with formation of an esterification mixture, (3) separation of the esterification mixture to obtain at least one fraction enriched with biodiesel and at least one fraction enriched with glycerol liberated in the esterification, and (4) if appropriate, conditioning the fraction enriched with glycerol. These processes are well known in the art. See US Patent Application 2007/099161.

The glycerol-containing stream of this invention is preferably added to the reactor in the liquid phase.

The hydrogenation is carried out using skeletal copper catalysts. The term "skeletal copper catalysts", as used herein and in the appended claims, means a porous catalytic alloy-based material comprising copper and aluminum. The alloy may further contain small amounts of other metals such as Cr, Mo, Co, Ni, Zn, Zr and the like. These metals are added as a promoter as described below. These porous materials, when microscopically viewed, take on a skeletal, sometimes referred to as a "sponge-like", appearance having tortuous pore channels throughout the particle. These high surface area products have been found to have sites for hydrogen activation and, thus, exhibit catalytic hydrogenation activity.

The porous catalyst is formed by using conventional metallurgical techniques to first form a precursor alloy of copper and aluminum (optionally having small amounts of up to about 10 weight percent of the aforementioned promoter metals, therein) in which the copper is present in from about 35 to 60 weight percent, with the remainder being primarily aluminum. The formed alloy is crushed and/or ground and classified by passing it through a sieve to provide a material having a desired size. Larger particles exiting the crushing or grinding mechanism can be recycled for further size reduction.

The formed alloy is then subjected to an aqueous alkali (e.g., sodium hydroxide) solution to extract the aluminum metal from the alloy. When granular, fixed bed type (cross sectional diameter of about 1 to 8 mm) catalyst is desired, the aluminum is partially extracted ("leached"), to the extent of leaching 20%-80%, preferably 40-60%, and more preferably at least 50% of the aluminum (Al) originally present, to obtain a final catalyst composition with about 10 to 60, preferably 20 to 40 weight percent Al and the balance as copper and promoters if present. The skeletal copper catalyst can be formed according to the process described in U.S. Pat. Nos. 1,628,190; 1,915,473; 2,139,602; 2,461,396; and 2,977,327. The teachings of these patents are incorporated herein in their entirety by reference.

Catalysts designed for a slurry reactor are prepared using the above techniques, except that the particles are ground to be less than 500 microns, more typically less than 75 microns, and frequently, in the range of 10 to 50 microns. The leaching conditions described above also are chosen to leave a catalyst having lower aluminum amounts, e.g., 1 to 10% aluminum, and more desirably 2 to 5% by weight aluminum.

Skeletal copper catalysts made in the above manner are well known, and are part of a family of metal alloy derived products sold by W. R. Grace & Co.-Conn. under the trademark RANEY®.

The alkali solution used to leach out the aluminum metal present is from either an inorganic (preferred) or organic compound. Conventional processes utilize an aqueous solution having from about 2 to 35 weight percent concentration of an alkali metal hydroxide (e.g., sodium hydroxide) employed as the leaching agent, preferably 5 to 10% by weight for a fixed bed catalyst, or preferably 20-30% for a slurry catalyst, from which a much larger fraction of aluminum is extracted. The alloy is usually treated at elevated temperatures of from about 30° C. to 110° C., preferably 30 to 60° C. for fixed bed catalysts and 60 to 100° C. for slurry catalysts. Alloy particles being processed for fixed bed catalysts sit in a vessel through which the alkali is pumped and/or re-circulated. For alloys processed for slurry activation, the alkali solution is stirred and the alloy powder can be directly added to the alkali solution, or it can be formed into an aqueous suspension, which is then contacted with the alkali solution. The aluminum contained in the alloy dissolves to form an alkali metal aluminate (e.g., sodium aluminate) with vigorous evolution of hydrogen. If silicon is also present in the alloy, the base forms the corresponding alkali metal silicate. The powder and alkali are normally allowed to remain in contact with each other for several hours at elevated temperature (e.g., 40°-60° C.) until the aluminum (or silicon) content is reduced to the desired level. Indeed, it has been determined for this invention that the fixed bed skeletal metal copper catalyst can be advantageously prepared using relatively high or "aggressive" leaching conditions in terms of temperature and residence time in the leaching bath. Preferred leaching conditions include those that can remove at least 40% or more of the aluminum originally present in a reasonably short batch time, e.g. greater than 8% NaOH solution applied at greater than 40° C. for 90 minutes or more. More extensive leaching leads to a porosity that has a higher sustainable rate of conversion of glycerol when the catalyst is used in a fixed bed process. The term "fixed bed", as used herein, refers to a mass of catalyst which is packed in a constrained static bed within a catalytic reactor, and through which the reactant mixture moves continuously, as opposed to a stirred or fluidized bed ("slurry" system) which moves constantly within a reactor, along with the reactant mixture.

The skeletal metal catalyst after activation is separated from the reaction liquor and then conventionally washed with water until the wash water has a slightly alkaline pH value of about 8 to 9. The pore volume, pore size and surface area of the catalyst will depend upon the amount of aluminum (or silicon) in the initial alloy and the degree of leaching.

The skeletal copper catalyst is promoted with from about 0.1 and about to 15% by weight of a promoter transition metal, depending on the specific promoter metal. Such transition metals include those capable of promoting the hydrogenation performance of the copper catalyst, e.g. selectivity, conversion rate and stability against deactivation. The skeletal copper catalyst of this invention preferably has a promoter transition metal content in the range of about 0.1 to about 10%. In a preferred embodiment of the invention, the skeletal copper catalyst has a promoter transition metal content in the range of about 0.5 to about 5.0%.

Transition metals useful to promote the skeletal copper catalyst include, but are not limited to, transition metals (other than copper) in Groups 4, 6, 7, 8, 9, 10 and 12 of the Periodic Table of Elements, and combinations thereof. In a preferred embodiment of the present invention the promoter transition metals include, but are not limited to, nickel, cobalt, molybdenum, zinc, chromium, zirconium and combinations of two or more of the same. In a more preferred embodiment of the present invention, the promoter transition metals include, but are not limited to, cobalt, molybdenum, zirconium and combinations of two or more of the same.

The promoter transition metals are typically added to the catalyst as a component in the base alloy of copper and aluminum as mentioned above, but could also be added in the leaching solution used to remove aluminum from copper aluminum alloy, or in an impregnation or coating bath following activation. If added via the leaching solution, one can include therein, an amount of promoter precursor, e.g., chromium chloride or other Cr compound equivalent, to a metal: catalyst ratio of about 0.2 to 2% by weight, preferably 0.5 to 1.5% by weight.

When using the option of applying promoters to the surface of the catalyst after activation, surface deposition is conducted during a post-activation washing stage wherein the catalyst is contacted with a (usually alkaline-pH) salt solution, to achieve the same approximate ranges of promoter described above. This surface deposition can be done at a chosen pH in e.g. the range of 9-12 preferably 10-11. The catalyst is stored under water at an alkaline pH of usually 9-11. In another post leaching process, the metal can be plated onto the catalyst utilizing coating or plating techniques described in the U.S. Pat. No. 7,375,053, the contents of which are incorporated herein by reference.

The above catalysts are more efficiently utilized in continuous processes, including those using a fixed catalyst bed. A trickle-bed process can be used with a fixed catalyst bed. The catalysts utilized in conventional fixed bed processes can be in various forms, including, but not limited to, granules, spheres, pressed cylinders, tablets, lozenges, wagon wheels, rings, stars, or extrudates, such as solid extrudates, polylobal extrudates, hollow extrudates and honeycomb bodies.

The above catalysts can also be utilized in other processes such as those using a continuous stirred slurry tank reactor, or batch-wise slurry processes. The term "slurry process" is used to embrace both of the non-fixed bed processes. The catalysts in slurry processes are usually finely divided particulate having an average particle size mentioned above. Catalyst is generally added to the slurry reactor at a weight ratio of catalyst to reactant in the range of 1:30 to 1:4.

Excess hydrogen is preferably circulated in the hydrogenation process, it being possible for a small part to be discharged as waste gas for removing gaseous by product materials. The molar ratio of hydrogen to glycerol is preferably from 2:1 to 500:1, preferably from 3:1 to 100:1, and most preferably 10:1 to 50:1, which equates to about 2000-10,000 volume ratio.

It is possible to use one reactor or a plurality of reactors which can be connected in series or parallel to one another.

The temperature for the process of this invention is generally greater than about 250° C. In an embodiment of the invention, the temperature ranges from about 260° C. to about 320° C. In a preferred embodiment of the invention, the temperature for the process of the invention ranges from about 270° C. to about 310° C.

The reaction conditions is preferably selected to maintain a liquid to partially liquid mixture within the reactor, while the reactant mixture coming into the reactor is preferably a continuous liquid phase, which may be pumped into the reactor under pressure. Suitable reaction pressures for use in the present invention include a pressure that is less than 100 bar (i.e. less than about 1470 psig). In a preferred embodiment the reaction pressure is less than 60 bar (i.e. less than about 750 psig). In a more preferred embodiment of the invention, the reaction pressure ranges from about 10 bar to about 50 bar (i.e. from about 150 psig to about 750 psig).

The space velocity in a continuous process embodiment of the invention is preferably from 0.05 to 0.30, more preferably from 0.10 to 0.20 kg of glycerol to be hydrogenated per kg (catalyst) per h.

Surprisingly, the process of the present invention offers excellent conversion of glycerol. For purposes of the present invention, the term "conversion" is used herein to indicate the disappearance of the starting glycerol during a single pass through the reactor. In a preferred embodiment of the invention, the conversion of glycerol is at least 80% in a continuous fixed bed process. In a more preferred embodiment of the invention, the conversion of glycerol is at least 90% in a continuous fixed bed process.

In the most preferred embodiment of the invention, conversions of up to 100% are achievable. However, in the event of incomplete conversion, separation of product from glycerol is readily achieved and unreacted glycerol may be recycled to the hydrogenation stage, with relatively little processing. Accordingly, any glycerol recovered from the process may be subjected to further conditioning, including adsorption and other purification steps designed to remove impurities, e.g. catalyst fines, reactant impurities, and the like, that could affect the application in which the glycerol will be utilized.

The process of this invention is surprisingly highly selective for a liquid-phase organic product which comprises 1- and 2-propanol as the major components. As will be understood by one skilled in the art, selectivity will vary depending on feedstock, water content, temperature and/or pressure in the hydrogenation, and type of hydrogenation, e.g., slurry versus fixed bed reactor. In one embodiment of the invention, a fixed bed process using an un-promoted skeletal copper catalyst exhibits relatively high selectivity for 1- and 2-propanol. The selectivity of the invention for propanols, expressed as the overall yield of 1- and 2-propanol, is typically at least 15% by weight based on the total weight of the glycerol feed. In a more preferred embodiment of the invention, the selectivity for 1- and 2-propanol is at least 20 weight % based on the total weight of the glycerol feed. It is within the scope of the invention that selectivity yields of up to 30% or more can be achieved. The term "overall yield" is used herein to designate that per 100 lbs of glycerol feed introduced into the reactor at least 15 lbs of 1- and 2-propanol is recovered.

Other minor constituents in the organic products produced by the invention process, albeit preferably in relatively little amounts, can include methanol, ethanol, 1,3-propanediol, 1,2-propanediol, 1,2-ethanediol (ethylene glycol), acrolein, lactic acid, and hydrocarbons.

To further illustrate the present invention and the advantages thereof, the following specific examples are given. The examples are given as specific illustrations of the claimed invention. It should be understood, however, that the invention is not limited to the specific details set forth in the examples.

All parts and percentages in the examples, as well as the remainder of the specification, which refers to solid compositions or concentrations, are by weight unless otherwise specified. However, all parts and percentages in the examples as well as the remainder of the specification referring to gas compositions are molar or by volume unless otherwise specified.

Further, any range of numbers recited in the specification or claims, such as that representing a particular set of properties, units of measure, conditions, physical states or percentages, is intended to literally incorporate expressly herein by reference or otherwise, any number falling within such range, including any subset of numbers within any range so recited.

EXAMPLES

Example 1

An unpromoted 50% Cu-50% Al alloy was made by conventional melting and mixing techniques. The cooled alloy was crushed and sieved to 8-12 mesh size range (about 2 to about 3 mm particle diameters). The alloy was converted to a catalyst by Al leaching. 250 g of the 8-12 mesh alloy was placed in a vessel, through which 6.4 liters of a 6.5% aqueous NaOH solution was re-circulated at 45° C. for 50 minutes. The catalyst was then washed to a pH of 9 with water at 45° C.

The final composition of the catalyst was 65% Cu and 35% Al, which equates to leaching (removal) of 45% of the initial aluminum in the alloy. The catalyst was labeled "Catalyst A".

Example 2

A Cr- and Ni-promoted alloy with composition of 1.5% Cr, 2.8% Ni, 45.7% Cu and 50% Al was prepared and sized as described in Example 1. To prepare a catalyst by Al leaching, 300 g of the 8-12 mesh alloy was placed in a vessel, through which 5 liters of a 10% aqueous NaOH solution was re-circulated at 45° C. for 105 minutes. The catalyst was then washed to a pH of 9 with water at 45° C.

The final composition of the catalyst was 2.2% Cr, 4.2% Ni, 58.7% Cu and 34.6% Al, which equates to leaching (removal) of 47% of the initial aluminum in the alloy. The catalyst was labeled "Catalyst B".

Example 3

A Co-promoted alloy with composition of 2.8% Co, 47% Cu and 50% Al was prepared and sized as described in Example 1. To prepare a catalyst by Al leaching, 250 g of the 8-12 mesh alloy was placed in a vessel, through which 6.4 liters of a 6.5% aqueous NaOH solution was re-circulated at 45° C. for 50 minutes. After partial washing of the catalyst to pH 11, an additional promoter, Mo, was introduced by adding ammonium heptamolybdate to the wash water at equivalent of 0.5% of the catalyst wt. and maintaining contact of this Mo solution with the catalyst for 30 minutes before resuming washing. The catalyst was then washed to a final pH of 9 with water at 45° C.

The final composition of the catalyst was 3.8% Co, 0.5% Mo, 63.9% Cu and 31.6% Al, which equates to leaching (removal) of 54% of the initial aluminum in the alloy. The catalyst was labeled "Catalyst C".

Example 4

A Cr- and Ni-promoted alloy with composition of 0.75% Cr, 2.8% Ni, 46.5% Cu and 50% Al was prepared and sized as described in Example 1. To prepare a catalyst by Al leaching, 300 g of the 8-12 mesh alloy was placed in a vessel, through which 5 liters of a 10% aqueous NaOH solution was re-circulated at 45° C. for 105 minutes. After partial washing of the catalyst to pH 11, an additional promoter, Mo, was introduced by adding ammonium heptamolybdate to the wash water at equivalent of 0.5% of the catalyst wt. and maintaining contact of this Mo solution with the catalyst for 30 minutes before resuming washing with additional water. The catalyst was then washed to a final pH of 9 with water at 45° C.

The final composition of the catalyst was 1.0% Cr, 4.4% Ni, 0.5% Mo, 65.7% Cu and 28.5% Al, which equates to leaching (removal) of 60% of the initial aluminum in the alloy. The catalyst was labeled "Catalyst D".

The summary of catalyst compositions prepared are recorded in Table 1 below:

TABLE 1

| Summary of Catalyst Compositions | | |
| --- | --- | --- |
| Example | Catalyst Type | Composition |
| 1 | A | Cu |
| 2 | B | Cr—Ni—Cu |
| 3 | C | Mo—Co—Cu |
| 4 | D | Mo—Cr—Ni—Cu |

Example 5

Catalyst A as prepared in Example 1 was tested in a fixed bed tube reactor in trickle bed mode, said reactor having a ½" inner diameter. The packed volume of the catalyst occupied by the catalyst was 14 cc. The reaction pressure was 600 psi and the reaction temperature ranged from 210° C. to 310° C. The feed consisted of 50 wt % aqueous glycerin. The feed rate was 0.1 cc/min, 6.786 g aqueous feed/h (3.393 g glycerin/h). The hydrogen flow rate was 300 cc/min. and liquid hourly space velocity (LHSV) of glycerin was 0.192 $h^{-1}$.

The test procedure entailed placing the catalyst immersed in water into the reactor. Any free space in catalyst-charged reactor was purged of air using inert gas flow, then the reaction was run by flowing hydrogen and the water-glycerine feed solution over the catalyst. Before entering the reactor, the glycerine and the hydrogen flow was passed through a preheating box kept at 140° C. The reactor contained a back pressure regulator (BPR) at the exit line of the reactor which is set to the desired process pressure. The two flows entered the top of the reactor, and after efficient mixing through the fitted filters in the pre-heating zone, trickled through the catalyst bed. The reactant flow exited the reactor and entered the BPR to step down the pressure to ambient. After the BPR, the mixture passed through a condenser kept at 25° C. The gas phase was next passed through a liquid trap held at −36° C. to quench low boiling products carried with the hydrogen flow. The weight and the volume of the reaction solution collected over a given period of time was measured accurately and analyzed by GC for product distribution by the following methods:

Reagents and Chemicals:
Glycerin (Aldrich, 99%)
de-ionized water (Pharmco)
Dioxane (Accros)

Apparatus:
HP 5890 with FID detector and an electronic integration
Capillary column RTX1701, 60 m, 0.53 mm internal diameter and film thickness of 1 mkm.
Instrument Conditions:
Split vent: 50 ml/min
Air flow: 300 ml/min
Hydrogen flow: 30 ml/min
Head pressure: 15 psi
Signal range: 7
Injection volume: 0.5 mkl
Temperature program: Initial temperature 35 C, hold 4 min, ramp 15 C/min to 185 C, hold 10 min.
Injection and detector temp: 220 C and 260 C
Taken from sample solution 25 mkl, dissolved in 900 mkl water and 500 mkl IS solution. The IS solution was 1,4-Butanediol in Dioxane (10 mg/ml).

Product yields were calculated and expressed as weight % of the original glycerin feed and are recorded in Table 2 below. The net weight lost in transit from the feed to the accumulated products was assumed to be un-condensable compounds such as CO, $CO_2$ and methane. This was reported as 'Lost as vapor'. Because of these un-condensable byproducts and the loss of mass as oxygen in converting from glycerin to diols and mono-ols, the combined yields of useful products do not sum to 100.

TABLE 2

Product yields from Catalyst A (Cu)

Product yield, g/100 g glycerine introduced

| Temperature, deg C. | Unconverted glycerine | Lost as vapor | Ethanol | i-propanol | n-propanol | ethylene glycol | 1,2-Propanediol | 1,3-Propanediol |
|---|---|---|---|---|---|---|---|---|
| 210 | 0 | 7.9 | 0.1 | 0 | 0.3 | 1.8 | 81.5 | 0 |
| 230 | 0 | 7.4 | 0.4 | 0.2 | 0.9 | 1.0 | 81.1 | 0 |
| 250 | 0 | 9.9 | 1.6 | 0.9 | 3.4 | 1.2 | 75.5 | 0 |
| 270 | 0 | 18.9 | 3.5 | 3.9 | 12.3 | 0.0 | 45.1 | 0 |
| 290 | 0 | 28.2 | 5.7 | 7.9 | 21.3 | 0.0 | 11.1 | 0 |
| 310 | 0 | 34.6 | 6.6 | 10.3 | 24.2 | 0.0 | 0.2 | 0 |

Example 6

Catalyst B prepared as described in Example 2 above was tested in the same manner as described above in Example 5. Results were recorded in Table 3 below:

TABLE 3

Product yields from Catalyst B (Cr—Ni—Cu)

Product yield, g/100 g glycerine introduced

| Temperature, deg C. | Unconverted glycerine | Lost as vapor | Ethanol | i-propanol | n-propanol | ethylene glycol | 1,2-Propanediol | 1,3-Propanediol |
|---|---|---|---|---|---|---|---|---|
| 210 | 31.8 | 2.5 | 4.2 | 0 | 0 | 0.4 | 40.5 | 0 |
| 225 | 0 | 11.3 | 4.3 | 0 | 0 | 0.8 | 63.8 | 0 |
| 240 | 0 | 13.7 | 1.6 | 0 | 1.3 | 0.6 | 57.8 | 0 |
| 255 | 0 | 23.0 | 3.4 | 0 | 3.2 | 0 | 45.8 | 0 |
| 270 | 0 | 35.4 | 10.1 | 1.5 | 8.2 | 0 | 21.7 | 0 |
| 285 | 0 | 53.2 | 13.7 | 3.0 | 11.0 | 0 | 1.5 | 0 |
| 300 | 0 | 79.6 | 5.7 | 2.5 | 4.1 | 0 | 0.4 | 0 |

Example 7

Catalyst C prepared as described in Example 3 above was tested in the same manner as described above in Example 5. Results were as recorded in Table 4 below:

TABLE 4

Product yields from Catalyst C (Mo—Co—Cu)

Product yield, g/100 g glycerine introduced

| Temperature, deg C. | Unconverted glycerine | Lost as vapor | Ethanol | i-propanol | n-propanol | ethylene glycol | 1,2-Propanediol | 1,3-Propanediol |
|---|---|---|---|---|---|---|---|---|
| 210 | 0 | 7.9 | 0.3 | 0.1 | 0.9 | 1.1 | 80.3 | 0 |
| 230 | 0 | 9.7 | 0.7 | 0.6 | 2.3 | 0.6 | 70.1 | 0 |
| 250 | 0 | 16.4 | 2.0 | 2.6 | 9.9 | 0.2 | 46.8 | 0 |
| 270 | 0 | 27.7 | 4.0 | 7.1 | 19.2 | 0.0 | 14.4 | 0 |
| 290 | 0 | 37.7 | 3.7 | 8.1 | 16.4 | 0.0 | 0.3 | 0 |
| 310 | 0 | 36.2 | 3.1 | 7.5 | 10.1 | 0.0 | 0.2 | 0 |

Example 8

Catalyst D prepared as described above in Example 4 was tested in the same manner as described above in Example 5. Results were as recorded in Table 5 below:

TABLE 5

Product yields from Catalyst D (Mo—Cr—Ni—Cu)

Product yield, g/100 g glycerine introduced

| Temperature, deg C. | Unconverted glycerine | Lost as vapor | Ethanol | i-propanol | n-propanol | ethylene glycol | 1,2-Propanediol | 1,3-Propanediol |
|---|---|---|---|---|---|---|---|---|
| 210 | 0 | 9.0 | 0.6 | 0 | 0.3 | 0.5 | 76.2 | 0 |
| 230 | 0 | 11.2 | 1.5 | 0 | 1.5 | 0.0 | 71.2 | 0 |
| 250 | 0 | 22.3 | 6.0 | 1.1 | 6.3 | 0.0 | 41.7 | 0 |
| 270 | 0 | 42.0 | 13.7 | 3.7 | 17.6 | 1.3 | 3.8 | 0 |
| 290 | 0 | 70.0 | 6.5 | 2.9 | 6.9 | 0.8 | 0.4 | 0 |
| 310 | 0 | 90.3 | 0.0 | 1.4 | 0.0 | 0.0 | 0.0 | 0 |

Table 6 below details the summary of the testing of catalysts in accordance with the invention.

TABLE 6

Summary of Testing

| Catalyst | Temperature (° C.) | Iso- + n-Propanol Yield |
|---|---|---|
| A (Cu) | 290-310 | 29-34% |
| B (Cr—Ni—Cu) | 270-285 | 10-14 |
| C (Mo—Co—Cu) | 270-310 | 24-28% |
| D (Mo—Cr—Ni—Cu) | 270 | 21% |

The results clearly evidence the selectivity of the invention process to produce propanols from glycerol in high yields. Under combined conditions of glycerol water content, reaction temperature and reaction pressure in the presence of promoted or unpromoted skeletal copper catalyst, the process in accordance with the invention unexpectedly provided a combined yield of 1- and 2-propanol as the major liquid phase product. The unpromoted skeletal copper catalyst was the most selective for propanol. Optimum temperature varied depending upon the catalyst.

The invention claimed is:

1. A catalytic process for the hydrogenation of glycerol comprising
   a) obtaining a glycerol-containing stream having a water content of at least 30% by weight of the total glycerol containing stream;
   b) subjecting the glycerol-containing stream to hydrogenation in the liquid phase in a reactor in the presence of a skeletal copper catalyst at a reaction temperature of greater than 250° C., and a reaction pressure of less than 100 bar; and
   c) wherein a combined weight % yield of 1-propanol and 2-probanol of at least 15% based on the total weight of glycerol feed is obtained as a major product.

2. The catalytic process of claim 1 wherein the skeletal copper catalyst is promoted with at least one transition metal other than copper selected from the group consisting of Groups 4, 6, 7, 8, 9, 10 and 12 of the Periodic Table of Elements, and combinations thereof.

3. The catalytic process of claim 2 wherein the skeletal copper catalyst is promoted with a transition metal selected from the group consisting of nickel, cobalt, molybdenum, zinc, chromium, zirconium and combinations thereof.

4. The catalytic process of claim 1 wherein the reaction pressure is less than 60 bar.

5. The catalytic process of claim 4 wherein the reaction pressure ranges from about 10 bar to about 50 bar.

6. The catalytic process of claim 1 wherein the water content of the glycerol is at least 50% by weight based on the total weight of the glycerol feed.

7. The catalytic process of claim 1 wherein a glycerol conversion of at least 80% is obtained.

8. The catalytic process of claim 1 wherein the reactor is a fixed bed reactor.

9. The catalytic process of claim 8 wherein the reactor is operated in a continuous manner.

10. A process for the selective production of 1-propanol and 2-propanol from glycerol in which a feed comprising:
   contacting a glycerol containing feed as a liquid in a reactor with a hydrogen-containing gas;
   subjecting the feed to hydrogenation in the presence of a skeletal copper catalyst at a reaction temperature of greater than 250° C., and a reaction pressure of less than 100 bar, wherein the water content of the glycerol feed is at least 30% by weight of the total feed; and
   recovering 1- and 2-propanol as the major product.

11. The process of claim 10 wherein the skeletal copper catalyst is promoted with at least one transition metal other than copper selected from the group consisting of Groups 4, 6, 7, 8, 9, 10 and 12 of the Periodic Table of Elements, and combinations thereof.

12. The process of claim 11 wherein the skeletal copper catalyst is promoted with a transition metal selected from the group consisting of nickel, cobalt, molybdenum, zinc, chromium, zirconium and combinations thereof.

13. The process of claim 10 wherein the reaction temperature is from about 260° C. to about 320° C.

14. The process of claim 13 wherein the reaction temperature is from about 270° C. to about 310° C.

15. The process of claim 10 wherein the reaction pressure is less than 60 bar.

16. The process of claim 15 wherein the reaction pressure ranges from about 10 bar to about 50 bar.

17. The process of claim 10 wherein the water content of the glycerol is at least 50% by weight based on the total weight of the glycerol feed.

18. The catalytic process of claim 10 wherein a glycerol conversion of at least 80% is obtained.

19. The catalytic process of claim 10 wherein a combined weight % yield of 1-propanol and 2-propanol recovered is at least 15% based on the total weight of glycerol feed.

20. The catalytic process of claim 10 wherein the reactor is a fixed bed reactor.

21. The catalytic process of claim 20 wherein the reactor is operated in a continuous manner.

* * * * *